(12) United States Patent
Lauria et al.

(10) Patent No.: US 6,476,068 B1
(45) Date of Patent: Nov. 5, 2002

(54) PLATINUM DERIVATIVE PHARMACEUTICAL FORMULATIONS

(75) Inventors: Sara Lauria, Monza; Alessandro Martini, Milan; Cristina Ciocca, Motta Visconti, all of (IT)

(73) Assignee: Pharmacia Italia, S.p.A., Nerviano (IT)

( * ) Notice: Subject to any disclaimer, the term of this patent is extended or adjusted under 35 U.S.C. 154(b) by 0 days.

(21) Appl. No.: 10/010,122

(22) Filed: Dec. 6, 2001

(51) Int. Cl.<sup>7</sup> ............................................... A61K 31/28
(52) U.S. Cl. ...................................................... 514/492
(58) Field of Search ......................................... 514/492

(56) References Cited

U.S. PATENT DOCUMENTS

| | | | | |
|---|---|---|---|---|
| 4,169,846 A | | 10/1979 | Kidani et al. ................ | 260/429 |
| 5,041,578 A | * | 8/1991 | Khokhar ....................... | 556/137 |
| 5,288,887 A | * | 2/1994 | Khokhar et al. ............. | 514/184 |
| 5,290,961 A | | 3/1994 | Okamoto et al. ............ | 556/137 |
| 5,298,642 A | | 3/1994 | Tozawa et al. ............... | 556/137 |
| 5,318,962 A | * | 6/1994 | Khokhar et al. ............. | 514/184 |
| 5,338,874 A | | 8/1994 | Nakanishi et al. ........... | 556/137 |
| 5,420,319 A | | 5/1995 | Okamoto et al. ............ | 556/137 |
| 5,633,016 A | | 5/1997 | Johnson ....................... | 424/649 |
| 5,716,988 A | | 2/1998 | Ibrahim et al. .............. | 514/492 |
| 5,945,122 A | | 8/1999 | Abra et al. ................... | 424/450 |
| 5,959,133 A | | 9/1999 | Ohnishi ....................... | 556/137 |
| 6,008,395 A | * | 12/1999 | Kidani ......................... | 556/137 |
| 6,056,973 A | | 5/2000 | Allen et al. .................. | 424/450 |
| 6,063,780 A | | 5/2000 | Dexter et al. ................ | 514/243 |
| 6,066,666 A | | 5/2000 | Covey et al. ................ | 514/424 |
| 6,066,668 A | | 5/2000 | Hausheer et al. ........... | 514/492 |
| 6,153,646 A | * | 11/2000 | Kidani et al. ................ | 514/492 |
| 6,287,593 B2 | | 9/2001 | Cherian ....................... | 424/450 |
| 6,306,903 B1 | | 10/2001 | Anderson et al. ............ | 514/492 |

FOREIGN PATENT DOCUMENTS

| | | |
|---|---|---|
| EP | 0715854 A2 | 6/1996 |
| EP | 0715854 A3 | 6/1996 |
| EP | 1121117 A2 | 8/2001 |
| WO | 9412193 | 6/1997 |
| WO | 0021527 | 4/2000 |
| WO | 0115691 A1 | 3/2001 |
| WO | 0166102 A2 | 9/2001 |

OTHER PUBLICATIONS

Khokhar, et al., "Toxicity and efficacy studies on a series of lipid–soluable dineodecanoato (trans–R,R–and trans–S, S–1,2–diaminocyclohexane) platinum (II) complexes entrapped in liposomes", *Anti–Cancer Drugs,* vol. 3, pp. 95–100 (1992).

Bleiberg, "CPT–11 in Gastrointestinal Cancer", *European Journal of Cancer,* vol. 35, No. 3, pp. 371–379.

Wasserman, et al., "Oxaliplatin (L–OHP) and Irinotecan (CPT11) Phase I/II Studies: Results in 5 FU Refractory (FR) Colorectal Cancer (CRC) Patients (pts)", *Proc. Am. Soc. Clin. Oncol.,* 18, 35 Meet., 238a (1999).

Wasserman, et al., "Combination of Oxaliplatin Plus Irinotecan in Patients with Gastrointestinal Tumors: Results of Two Independent Phase I Studies with Pharmacokinetics", *Journal of Clinical Oncology,* vol. 16, No. 7, pp. 1751–1759 (1999).

Veal, et al., "A Phase I Study of Paediatric Patients to Evaluate the Safety and Pharmacokinetics of SPI–77, a Liposome Encapsulated Formulation of Cisplatin", *British Journal Of Cancer,* vol. 84 (8), pp. 1029–1035 (2001).

Curis, et al., "Carboplatin and Oxaliplatin Decomposition in Chloride Medium, Monitored by XAS", *J. Synchrotron Rad.,* vol. 8, pp. 716–718 (2001).

* cited by examiner

*Primary Examiner*—James H Reamer
(74) *Attorney, Agent, or Firm*—McDonnell Boehnen Hulbert & Berghoff

(57) ABSTRACT

The present invention relates to novel stable solution formulations comprising oxaliplatin, an effective stabilizing amount of lactic acid and/or a pharmaceutically acceptable salt thereof and a pharmaceutically acceptable carrier. A method for manufacturing such formulations ready for administration and their use in the antitumor therapy are also within the scope of the invention.

29 Claims, No Drawings

PLATINUM DERIVATIVE PHARMACEUTICAL FORMULATIONS

FIELD OF THE INVENTION

The present invention pertains to the field of pharmaceutical compositions for the treatment of neoplastic diseases and, particularly, it relates to pharmaceutical formulations comprising a platinum derivative.

SUMMARY OF THE INVENTION

The present invention is directed to novel stable formulations of oxaliplatin, wherein lactic acid and/or a pharmaceutically acceptable salt thereof serves as a novel means for preparing a dosage unit with an improved stability. A method for manufacturing such formulations ready for administration and their use in antitumor therapy are also within the scope of the invention.

BACKGROUND OF THE INVENTION

Oxaliplatin, also known as L-OHP, is a third generation platinum complex.

The term "oxaliplatin" as used herein, includes cis-oxalato(trans-l-1,2-diaminocyclohexane) platinum(II), its optic enatiomer cis-oxalato(trans-d-1,2-diaminocyclohexane) platinum(II) and any racemic mixture thereof. The term "oxaliplatin" also includes cis-oxalato (trans-l-1,2-diaminocyclohexane) platinum(II) having high optical purity, namely an optical purity equal to or higher than 99.5%, for example a cis-oxalato(trans-l-1,2-diaminocyclohexane) platinum(II), wherein the melting point is between 198° C. and 292° C., obtained following the procedure described in Tanaka U.S. Pat. No. 5,338,874 and, especially, a cis-oxalato (trans-l-1,2-cyclohexanediamine) platinum(II), which possesses optical purity of 99.94% or more and a melting point between 198.3° C. and 199.7° C., obtained following the procedure disclosed in Tanaka U.S. Pat. No. 5,420,319.

Oxaliplatin has entered clinical development and achieved approval for marketing. During its development, oxaliplatin has aroused lively interest due, firstly, to its in vitro and in vivo antitumoral activity, especially in cisplatin-resistant models and cell lines expressing resistance genes, and, secondly, to its good clinical tolerance, the absence of renal or auditory toxicity being combined with a low hematotoxicity. Combined with other antitumoral agent cytotoxic agents (5-FU, raltitrexed, irinotecan or cisplatin), oxaliplatin produces an additive and often synergistic cytotoxic effect. The oxaliplatin-5FU+FA combination is now well established in the treatment of metastatic colorectal cancer. Regarding its particular cytotoxic characteristics and its activity in mismatch repair deficient cells (which are resistant to cisplatin and carboplatin), oxaliplatin has shown potential in a large variety of solid tumor types, notably in association with other cytotoxic agents, thus opening the path to a wider range of indications.

Kidani et al., U.S. Pat. No. 4,169,846, discloses cis-platinum(II) complexes of 1,2-diaminocyclohexane active as antitumor compounds. Cis-oxalato(trans-l-1,2-diaminocyclohexane)platinum(II) is specifically disclosed in Example 4(i).

SmithKline Beecham, U.S. Pat. No. 5,633,016, discloses a method for inhibiting tumor cell growth using synergistic combination of a camptothecin analogue and a platinum coordination compound, e.g. cisplatin and oxaliplatin.

Tanaka, U.S. Pat. No. 5,290,961, discloses a process for preparing various platinum compounds including oxaliplatin, which comprises adding silver ion solution to cis-platinum (II) di halogen compound, filtering of silver halide, adding iodide compound and active carbon then adding organic di basic acid.

Tanaka, U.S. Pat. Nos. 5,338,874, 5,298,642 and 5,420,319, disclose optically pure oxaliplatin and methods for preparing the same.

Debiopharm, International patent application WO 94/12193, discloses a freeze-dried composition for jointly administering cisplatin and oxaliplatin.

Tanaka, U.S. Pat. No. 5,420,319, discloses oxaliplatin having high optical purity and a process for obtaining it.

Debiopharm, U.S. Pat. No. 5,716,988, discloses a stable oxaliplatin preparation for parenteral administration comprising an aqueous solution of oxaliplatin, in a concentration of 1 to 5 mg/ml, and with a pH in the range of 4.5 to 6.

Tanaka, European patent application No. 715,854, discloses a combination of: (a) at least one of cisplatin, carboplatin, 5-fluorouracil (5-FU), tegaful, carmoful, doxifluridine, uracil, irinotecan, adriamycin, etoposide, mitomycin, mitoxantrone and bleomycin; and (b) oxaliplatin, which produces an additive or synergistic effect on killing cells during cancer therapy.

Tanaka, U.S. Pat. No. 5,959,133, discloses a high-yielding process for obtaining chelating platinum complexes including oxaliplatin, which does not contain dihydroxoplatinum complex impurity.

Pharmacia & Upjohn Co., U.S. Pat. No. 6,287,593, discloses a phospholipid complex of a platinum dicarboxylate including oxaliplatin, which can be reconstituted in a pharmaceutically acceptable vehicle with or without lyophilization and administered to a mpatient in the treatment of cancer and other diseases.

Debiopharm, European patent application No. 1121117 discloses a liquid pharmaceutical preparation of oxaliplatin packaged in a container, preferably in a sealed soft bag for medical use. The liquid preparation of oxaliplatin can advantageously be presented in the form of a bag with several compartments containing doses of a ready-to-use solution.

Sanofi-Synthelabo, U.S. Pat. No. 6,063,780, discloses a treatment of mammalian solid tumors with the co-administration of 3-amino-1,2,4-benzotriazine 1,4-dioxide (tirapazamine) paclitaxel and oxaliplatin.

Debiopharm, International patent application No. WO 01/15691, discloses stable solutions of oxaliplatin, ready for parenteral administration, containing 1,2-propane diol, glycerol, maltitol, sucrose, and/or inositol.

BioNumerik, U.S. Pat. No. 6,066,666, discloses pharmaceutical formulations comprising a platinum analogue compound, e.g. oxaliplatin and a protective agent having either a sulfhydryl moiety or being reducible disulfide.

Bristol-Myers Squibb, International patent application WO 01/66102 discloses oral dosage forms for administration of the combination of tegafur+uracil (UFT), folinic acid, and oxaliplatin and methods of using the same.

Sanofi-Synthelabo, U.S. Pat. No. 6,306,902, discloses a stable oxaliplatin solution formulation comprising a therapeutically effective amount of oxaliplatin, an effective stabilizing amount of a buffering agent and a pharmaceutically acceptable carrier wherein the buffering agent is oxalic acid or an alkali metal salt thereof.

Bissery M. C., U.S. patent application Ser. No. 2001/0041712, discloses compositions and methods for treating tumors comprising administering CPT-11 with oxaliplatin.

At present, oxaliplatin is solely marketed in the form of lyophilized preparations, which need to be reconstituted before administration. The currently marketed formulation is a lyophilized powder (50, 100 mg) to be reconstituted just before administration to a patient with water for injection or a 5% glucose solution and finally diluted with a 5% glucose solution (0.2 mg/ml final concentration).

The lyophilized oxaliplatin can present some disadvantages, which do not render particularly attractive the use of this product in such a pharmaceutical form.

Both the manufacturing and the reconstitution of such preparations expose the involved personnel (workers, pharmacists, medical personnel, nurses) to risks of contamination, which are particularly serious due to the toxicity of the antitumor substances. To administer a lyophilized preparation, double handling of the drug is required, the lyophilized cake having to be first reconstituted and then administered and, moreover, in some cases, the complete dissolution of the powder may require shaking.

The risks connected with the manufacturing and the reconstitution of a lyophilized preparation would be highly reduced if a ready-to-use (RTU) solution of oxaliplatin, whose preparation and administration does not require either lyophilization or reconstitution, were available.

In order to meet the need for solution formulations of oxaliplatin in a RTU form, able to overcome the above-described disadvantages, some formulations have been already proposed, e.g., the Debiopharm and Sanofi-Synthelabo RTU formulations disclosed in the U.S. Pat. Nos. 5,716,988 and 6,306,902, respectively. Both these formulations are reported to be stable RTU formulations containing oxalipatin.

A desirable objective is therefore that the stability is further enhanced, and also that dosage forms can be suitably kept for a prolonged period.

The present invention meets these objectives by providing oxaliplatin formulations in a RTU form, with superior stability properties versus the above-identified known RTU preparations. It has now surprisingly been found that the introduction of lactic acid and/or a pharmaceutically acceptable salt thereof as a stabilizing agent in an aqueous solution of oxaliplatin, serves as a novel method of making a formulation with an improved stability versus both the RTU aqueous formulation disclosed in the Debiopharm U.S. Pat. No. 5,716,988 and the aqueous solution stabilized with oxalic acid or an alkali metal salt thereof, disclosed in the Sanofi-Synthelabo U.S. Pat. No. 6,306,902.

DETAILED DESCRIPTION OF THE INVENTION

It is an object of the present invention to provide a stable oxaliplatin solution formulation comprising a formulation selected from the group consisting of (a) oxaliplatin, an effective stabilizing amount of lactic acid, and a pharmaceutically acceptable carrier; (b) oxaliplatin, an effective stabilizing amount of a pharmaceutically acceptable salt of lactic acid, and a pharmaceutically acceptable carrier; and (c) oxaliplatin, an effective stabilizing amount of lactic acid and a pharmaceutically acceptable salt of lactic acid, and a pharmaceutically acceptable carrier.

The novel oxaliplatin formulations according to the invention have substantially improved storage stability when compared with the closest known formulations.

No prior art of which applicants are aware describes oxaliplatin formulations as now provided herein.

To the best of applicants' knowledge, the oxaliplatin pharmaceutical formulations of the invention are previously unknown and are not suggested by the art.

A pharmaceutically acceptable salt of lactic acid is, e.g., an alkali metal salt thereof such as, e.g. sodium or potassium, especially sodium lactate.

In a preferred embodiment, the present invention provides a stable oxaliplatin solution formulation comprising oxaliplatin, an effective stabilizing amount of lactic acid and a pharmaceutically acceptable carrier.

In a more preferred embodiment, the invention provides a stable oxaliplatin solution formulation comprising oxaliplatin, an effective stabilizing amount of lactic acid and water as a carrier.

In another aspect, the invention relates to a stable oxaliplatin solution formulation comprising oxaliplatin, an effective stabilizing amount of a pharmaceutically acceptable salt of lactic acid, and a pharmaceutically acceptable carrier.

In a preferred aspect, the invention relates to a stable oxaliplatin solution formulation comprising oxaliplatin, an effective stabilizing amount of an alkali metal salt of lactic acid, and a pharmaceutically acceptable carrier.

In a more preferred aspect, the invention relates to a stable oxaliplatin solution formulation comprising oxaliplatin, an effective stabilizing amount of sodium lactate and a pharmaceutically acceptable carrier.

More particularly, the invention relates to a stable oxaliplatin solution formulation comprising oxaliplatin, an effective stabilizing amount of sodium lactate and water as a carrier.

A further aspect the invention relates to a stable oxaliplatin solution formulation comprising oxaliplatin, an effective stabilizing amount of lactic acid and a pharmaceutically acceptable salt thereof, and a pharmaceutically acceptable carrier.

The present invention also encompasses a stable oxaliplatin solution formulation as defined above wherein oxaliplatin is, particularly, cis-oxalato(trans-l-1,2-diaminocyclohexane)platinum(II), more particularly, cis-oxalato(trans-l-1,2-diaminocyclohexane)platinum(II) having high optical purity, still more particularly, cis-oxalato(trans-l-1,2-diaminocyclohexane)platinum(II) having a melting point between 198° C. and 292° C. and cis-oxalato(trans-l-1,2-diaminocyclohexane)platinum(II) possessing optical purity equal to or higher than 99.94% such as, for example, cis-oxalato(trans-l-1,2-diaminocyclohexane)platinum(II) having a melting point between 198.3° C. and 199.7° C.

A method for stabilizing a formulation of oxaliplatin, which comprises adding an effective stabilizing amount of lactic acid and/or a pharmaceutically acceptable salt thereof to an aqueous carrier and then dissolving oxaliplatin in said carrier, is also within the scope of the present invention.

A pharmaceutically acceptable carrier according to the invention can be water or any solution containing water and additional solvents that are soluble/miscible in water, such as, for example, ethanol, glycerin, propylene glycol and polyoxyethylenglycols, and additional excipients that provide isotonicity to the formulation, such as, for example, dextrose or saline. Preferably, the carrier is water.

The amount of oxaliplatin present in a formulation according to the invention can range from 0.1 mg/ml to 10 mg/ml, preferably from 2 mg/ml to 5 mg/ml.

The stabilizing amount of the lactic acid and/or a pharmaceutically acceptable salt thereof can range from a molar concentration of $5.10^{-7}$ M to 1 M, preferably it can range from $5.10^{-5}$ M to $5.10^{-3}$ M.

The pH of the oxaliplatin solution formulations can range from about 3 to about 9, preferably from 3 to 7.

A formulation according to the invention can be prepared by a process comprising the steps of preparing an aqueous carrier with the appropriate amount of the lactic acid and/or the pharmaceutically acceptable salt, and then dissolving oxaliplatin into said carrier.

Preferably the solution of the invention is provided in a sealed container.

A further object of this invention comprises the use of a formulation according to the invention for the treatment of a cancer.

A method for treating a cancer which comprises administering a formulation according to the invention to a patient in need thereof is also within the scope of the present invention.

The term "treating" as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

In the above methods, the effective dosage of oxaliplatin to be administered to a patient ranges from about 10 mg/m$^2$ to about 250 mg/m$^2$, more preferably from about 30 mg/m$^2$ to about 180 mg/m$^2$ and most preferably is about 85 mg/m$^2$. However, it will be understood that the therapeutic dosage administered will be determined by the physician in the light of the relevant circumstances including the severity of the condition to be treated and the chosen route of administration. Therefore, the above dosage ranges are not intended to limit the scope of the invention in any way.

It is also an aspect of this invention that a formulation described herein, can be combined with other chemotherapeutic agents for the treatment of the diseases and disorders discussed above. For instance, a formulation according to the invention can be combined with alkylating agents such as fluorouracil (5-FU) alone or in further combination with leukovorin; or other alkylating agents such as, without limitation, other pyrimidine analogs such as UFT, capecitabine, gemcitabine and cytarabine; the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma). Likewise the formulation of the invention can be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias. The formulation according to the present invention can also be expected to prove efficacious in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposils sarcoma; the antibiotic chemotherapeutic agents, e.g., daunorubicin, doxorubicin, epirubicin, idarubicin, and mitomycin (used to treat stomach, cervix, colon, breast, bladder and pancreatic cancer), dactinomycin, temozolomide, plicamycin, bleomycin (used in the treatment of skin, esophagus and genitourinary tract cancer); nemorubicin and the enzymatic chemotherapeutic agents such as L-asparaginase. In addition to the above, the formulation of the present invention can be expected to have a beneficial effect used in combination with other platinum coordination complexes, e.g., cisplatin and carboplatin; substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors (such as, e.g., formestane, fadrozole, letrozole, anastrozole and exemestane).

A formulation according to the invention can also be active in combination with a topoisomerase I inhibitor such as, e.g., irinotecan (CPT-11), topotecan, rubitecan and lurtotecan.

The following examples illustrate but do not limit in any way the invention. All references cited herein are incorporated in their entirety.

EXAMPLES

Example 1

Preparation of Oxaliplatin Solutions

Solutions have been prepared by the following procedure:

Prepare the aqueous carrier weighting an appropriate amount of organic acid or one of its related salts in order to reach the established molarity; add water for injection to make up to the final volume.

Weigh Oxaliplatin into a suitable container and add the appropriate volume of an aqueous carrier in order to reach, as an example, 2 mg/ml as final concentration.

Dissolution of the active compound in the aqueous carrier easily occurs by a simple magnetic stirring or sonication.

The following formulations, as in Table 1, have been prepared.

TABLE 1

| | Non active ingredient (3) | oxaliplatin concentration | pH |
|---|---|---|---|
| FORMULATION 1 | Water for inj. | 2 mg/ml | 6.7 |
| FORMULATION 2 | Sodium oxalate 0.0005 M | 2 mg/ml | 7.1 |
| FORMULATION 3 | Lactic acid 0.0004 M | 2 mg/ml | 3.7 |
| FORMULATIQN 4 | Acetate 0.1 M | 2 mg/ml | 4.5 |
| FORMULATION 5 | Citrate 0.1 M | 2 mg/ml | 5.1 |

FORMULATION 1 is a representative example of the formulations described in Debiopharm's U.S. Pat. No. 5,716,988.

FORMULATION 2 is a representative example of the formulations described in Sanofi-Synthelabo's U.S. Pat. No. 6,306,902.

FORMULATION 3 is a representative example of a formulation according to the invention.

FORMULATION 4 and FORMULATION 5 are reference formulations described in Sanofi-Synthelabo's U.S. Pat. No. 6,306,902.

Example 2

Stability Study

The above-mentioned formulations in Example 1 have been investigated by an accelerated stability study and the chemical assay of the active compound has been tested by high performance liquid chromatography (HPLC) after 1 and 3 months of storage at 40° C. and 75% relative humidity.

Results, expressed as percentage of the weighted amount of the active compound, are summarized in Table 2.

TABLE 2

|  | 1 month | 3 months |
| --- | --- | --- |
| FORMULATION 1 | 97.1 | 61.9 |
| FORMULATION 2 | 97.5 | 95.4 |
| FORMULATION 3 | 100.0 | 99.5 |
| FORMULATION 4 | 100.5 | 69.2 |
| FORMULATION 5 | 28.5 | Not determined |

The above-tabulated data clearly demonstrate that:

a simple oxaliplatin water solution is not stable after 3 months storage at the the tested conditions;

lactic acid formulation has showed a stabilizing capacity on the active compound that is more effective than all the other mono and bi-organic acids tested.

Example 3

Stability Study

A second chemical stability study has been performed on the following formulations here mentioned in Table 3 and prepared by the procedure illustrated in Example 1.

The aim of this second study is to evaluate the stabilizing effect of different concentrations of lactic acid and sodium lactate and different pH on the active compound.

TABLE 3

|  | Non active ingredients | oxaliplatin concentration | pH |
| --- | --- | --- | --- |
| FORMULATION 6 | Lactic Acid 0.005 M | 2 mg/ml | 3.1 |
| FORMULATION 7 | Lactic Acid 0.0005 M | 2 mg/ml | 3.8 |
| FORMULATION 8 | Lactic Acid 0.0001 M | 2 mg/ml | 4.7 |
| FORMULATION 9 | Lactic Acid 0.00005 M | 2 mg/ml | 5.1 |
| FORMULATION 10 | Sodium Lactate 0.005 M | 2 mg/ml | 6.3 |

The obtained results are summarized in the following Table 4 and show how even very low amounts of lactic acid and sodium lactate have a stabilizing capacity on an oxaliplatin water solution.

TABLE 4

|  | 1 month | 2 months |
| --- | --- | --- |
| FORMULATION 6 | 99.5 | 99.0 |
| FORMULATION 7 | 101.4 | 99.5 |
| FORMULATION 8 | 99.5 | 99.5 |
| FORMULATION 9 | 103.0 | 106.0 |
| FORMULATION 10 | 98.0 | 100.5 |

What is claimed is:

1. Stable oxaliplatin solution formulation comprising a formulation selected from the group consisting of:
   (a) oxaliplatin, an effective stabilizing amount of lactic acid, and a pharmaceutically acceptable carrier;
   (b) oxaliplatin, an effective stabilizing amount of a pharmaceutically acceptable salt of lactic acid, and a pharmaceutically acceptable carrier; and
   (c) oxaliplatin, an effective stabilizing amount of lactic acid and a pharmaceutically acceptable salt of lactic acid, and a pharmaceutically acceptable carrier.

2. Stable oxaliplatin solution formulation comprising oxaliplatin, an effective stabilizing amount of lactic acid and a pharmaceutically acceptable carrier.

3. A formulation as claimed in claim 1, wherein the pharmaceutically acceptable salt of lactic acid is an alkali metal salt.

4. A formulation as claimed in claim 3 wherein the alkali metal salt of lactic acid is sodium lactate.

5. A formulation according to claim 1, wherein the carrier is water.

6. A formulation according to claim 2 wherein the carrier is water.

7. A formulation according to claim 3 wherein the carrier is water.

8. A formulation according to claim 4, wherein the carrier is water.

9. A formulation as claimed in claim 1, wherein the effective stabilizing amount of lactic acid and/or a pharmaceutically acceptable salt thereof ranges from a molar concentration of $5.10^{-7}$ M to 1 M.

10. A formulation as claimed in claim 9, wherein the effective stabilizing amount of lactic acid and/or a pharmaceutically acceptable salt thereof ranges from a molar concentration of $5.10^{-5}$ M to $5.10^{-3}$ M.

11. A formulation as claimed in claim 2, wherein the effective stabilizing amount of lactic acid ranges from a molar concentration of $5.10^{-7}$ M to 1 M.

12. A formulation as claimed in claim 11, wherein the effective stabilizing amount of lactic acid ranges from a molar concentration of $5.10^{-5}$ M to $5.10^{-3}$ M.

13. A formulation as claimed in claim 12, wherein the effective stabilizing amount of lactic acid is $4.10^{-4}$ M.

14. A formulation as claimed in claim 1, wherein the pH of the solution ranges from 3 to 9.

15. A formulation as claimed in claim 14, wherein the pH of the solution ranges from 3 to 7.

16. A formulation as claimed in claim 2, wherein the pH of the solution ranges from 3 to 9.

17. A formulation as claimed in claim 16, wherein the pH of the solution ranges from 3 to 7.

18. A formulation as claimed in claim 1, wherein the amount of oxaliplatin ranges from 0.1 mg/ml to 10 mg/ml.

19. A formulation as claimed in claim 18, wherein the amount of oxaliplatin ranges from 2 mg/ml to 5 mg/ml.

20. A formulation as claimed in claim 2, wherein the amount of oxaliplatin ranges from 0.1 mg/ml to 10 mg/ml.

21. A formulation as claimed in claim 20, wherein the amount of oxaliplatin ranges from 2 mg/ml to 5 mg/ml.

22. A formulation as claimed in claim 1, for use in the treatment of a cancer.

23. A method for treating a cancer, which comprises administering a formulation as claimed in claim 1 to a patient in need thereof.

24. A method for stabilizing a formulation of oxaliplatin, which comprises adding an effective stabilizing amount of lactic acid or a pharmaceutically acceptable salt thereof or both to an aqueous carrier and then dissolving oxaliplatin in said carrier.

25. A formulation as claimed in claim 1, wherein oxaliplatin is cis-oxalato(trans-l-1,2-diaminocyclohexane)platinum(II).

26. A formulation as claimed in claim 1, wherein oxaliplatin is cis-oxalato(trans-l-1,2-diaminocyclohexane)platinum(II) having high optical purity.

27. A formulation as claimed in claim 26, wherein the melting point of cis-oxalato(trans-l-1,2-diaminocyclohexane)platinum(II) is between 198° C. and 292° C.

28. A formulation as claimed in claim 26, wherein the cis-oxalato(trans-l-1,2-diaminocyclohexane)platinum(II) possesses optical purity equal to or higher than 99.94%.

29. A formulation as claimed in claim 28, wherein the melting point of the cis-oxalato(trans-l-1,2-diaminocyclohexane)platinum(II) is between 198.3° C. and 199.7° C.

* * * * *